(12) United States Patent
Henning et al.

(10) Patent No.: US 6,583,627 B2
(45) Date of Patent: Jun. 24, 2003

(54) PROCESS AND APPARATUS FOR TESTING MULTI-LAYER COMPOSITES AND CONTAINERS PRODUCED THEREFROM

(75) Inventors: Carsten Henning, Recklinghausen (DE); Matthias Hausmann, Dortmund (DE); Juergen Wittekind, Frankfurt (DE); Andreas Kuehnel, Oberursel (DE); Heinrich Kladders, Muelheim (DE); Heiko Rengel, Ober-Olm (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 33 days.

(21) Appl. No.: 10/028,600

(22) Filed: Dec. 20, 2001

(65) Prior Publication Data

US 2002/0116985 A1 Aug. 29, 2002

(30) Foreign Application Priority Data

Dec. 21, 2000 (DE) .......................................... 100 63 833

(51) Int. Cl.[7] .......................... G01N 27/62; G01R 31/08
(52) U.S. Cl. .......................... 324/464; 324/459; 324/514
(58) Field of Search ................................. 324/462, 464, 324/470, 514, 557, 556, 559, 718, 459; 73/49.2, 52, 40.7, 705, 49.3; 340/605, 632; 206/438, 524.1; 53/400, 401, 402, 428, 403, 79, 53, 507, 508

(56) References Cited

U.S. PATENT DOCUMENTS 6,314,796 B1 * 11/2001 Wittekind et al. ........... 73/49.2
6,448,777 B1 *  9/2002 Abdel-Rahman et al. ... 324/464

* cited by examiner

*Primary Examiner*—N. Le
*Assistant Examiner*—Donald M Lair
(74) *Attorney, Agent, or Firm*—Robert P. Raymond; Mary-Ellen M. Devlin; Alan R. Stempel

(57) ABSTRACT

The invention relates to a process and an apparatus for detecting gas-permeable damaged points in an electrically non-conductive layer which can exist as a single layer or as a multi-layer composite with at least one conductive layer, which process can be used for containers or packaging of pharmacological preparations to determine their integrity after storage.

27 Claims, 2 Drawing Sheets

PROCESS AND APPARATUS FOR TESTING MULTI-LAYER COMPOSITES AND CONTAINERS PRODUCED THEREFROM

IN THE SPECIFICATION

BACKGROUND OF THE INVENTION

The invention relates to a process for testing multi-layer composites, for example metal-plastic composite films, and containers produced therefrom. Furthermore, the invention relates to an apparatus which is suitable for implementing the process.

The aim of the invention is to specify a process via which damaged points can be identified with great sensitivity in a layer which is not electrically conductive, this process being suitable for large-scale manufacture.

The expression "damaged point" designates an area of the layer which is not electrically conductive, whose size is in the microscopic or sub-microscopic range and which is more pervious for molecules of a material than the diffusion constant of the material in the present layer which does not have such a damaged point.

Metal-plastic composites or composites of an electrically-conductive plastic and an electrically non-conductive plastic, or form-stable containers coated on the inside with an electrically non-conductive plastic are used for packaging which is to protect the packaged products, for example foodstuffs or pharmaceutical preparations in fluid or solid form to some special degree, for example against the inward diffusion of air, against moisture in the air, against light or against the loss by diffusion of volatile contents from the packaging.

Composites of this type comprise a thin metal foil, generally aluminium foil, which is generally coated on both sides with one or more plastic films. Generally, one side of the aluminium foil is provided with a sealable layer which permits hermetically-sealed containers to be produced from such composites, for example packaging bags.

Pure plastic films are generally permeable to gases and steam. However, composite films of metal and plastic are practically diffusion-proof. In the case of containers produced from such composite films, the diffusion is generally determined by the quality of the seam.

In order that the composite films are sufficiently flexible, the individual films, especially the plastic inner film which faces the packaged product, are kept very thin. When processing into corresponding containers, these thin interior films can easily be damaged and at gas-permeable damaged points in the inner film, contact may occur between the metal foil which lies under the inner film and the packaged product. In the case of sensitive products, this metal contact can affect the packaged product. Furthermore, the packaged product can destroy the metal foil by corrosion, whereupon the composite film looses its proof against diffusion.

A plurality of processes are known for testing whether a composite is undamaged and that the integrity of seals on containers produced from, or comprising, such a composite is not jeopardised. In the case of one widely-used process, the filled and sealed container is placed in a chamber which is at reduced pressure, this chamber being provided with a sensitive manometer, and also being connected with a vacuum pump via a valve. When the reduced-pressure chamber is evacuated to a specified pressure and the valve closed, if a seal of the container fails a part of the contents leaves the container and evaporates corresponding to its vapour pressure in a vacuum, whereupon the pressure shown on the manometer increases. The pressure shown on the manometer can be used as an indicator for a failed seal.

DE-196 51 208 describes a test process wherein the brightness of a gas discharge in a vacuum is used as an indicator for the quantity of leakage leaving a filled container.

In the case of another very sensitive process, helium is charged into the container. The helium leaving the closed container is detected with a mass spectrometer.

With another process, plastic coatings on metal surfaces are tested for pore freedom. Here, the metal surface is connected with a terminal of a voltage source. A flexible electrode, which can comprise, for example, an electrically-conductive elastomer, is connected via a measuring device to the other terminal of the voltage source. The coated surface which is to be tested is scanned with the flexible electrode. If there is a damaged point in the coating between the flexible electrode and the conductive substrate, electrical current flows into the circuit which serves as an indicator for the gas-permeable damaged point.

According to a further process, the plastic coating on a metal surface which is to be tested is wetted with an electrolyte in which an electrode is submerged. The other electrode is formed by the metal surface. Both electrodes are placed in an electrical circuit which contains a measuring device and a voltage source. If there is a damaged point in the area of the coating which is wetted with the electrolyte, an electrical current flows in the circuit which is provided with a voltage source, this current serving as an indicator for the damaged point. The metal foil is used as the electrode in the case of composite films of plastic and metal.

Form-stable containers with an electrically-insulating inner layer can be tested in a similar manner. Here, the container is filled with an electrolyte in which an electrode is submerged.

Scanning the surface with an electrode is only possible with flat or slightly-bent and accessible surfaces. Small containers can not be tested in this manner.

When using an electrolyte, small containers can also be tested. Containers which are tested and found to be trouble-free should, however, be carefully cleaned and dried, wherein the examination of large numbers of containers is made very difficult. In the case of miniaturised and sterilised disposable containers for pharmaceutical products, scanning processes and electrolyte processes are not practicable.

Hence the object is to specify a process and an apparatus for detecting gas-permeable damaged points in test subjects which comprise an electrically non-conductive layer, wherein the electrically non-conductive layer is opposite an electrically-conductive layer on the one side and on the other side is opposite a gas environment. The test subjects can be present as an individual electrically non-conductive layer or as a multi-layer composite, or as containers produced therefrom.

With the process, the undamaged nature of the electrically non-conductive layer and the soundness of containers produced from the electrically non-conductive layer or from the multi-layer composite can be tested, and this is also the case if only one of the non-conductive layers in a multi-layer composite is damaged. The process should also be applicable for miniaturised containers and larger production runs, and should take place automatically if possible.

This object is solved by a process having the following characterising features. At least one test subject is disposed in a test chamber which has been evacuated to a given pressure and is maintained at this pressure. The gas in the gas environment is ionised by means of an electrical gas discharge on the other side of the electrically non-conductive layer, preferably by impact-ionisation during dark discharge. An electrical voltage is applied between the electrically-conductive layer which lies on the other side of the electrically non-conductive layer, and a counter-electrode disposed in the test chamber, this electrical voltage generating a field strength in the area of the electrically non-conductive layer which lies beneath the dielectric strength of the electrically non-conductive layer without gas-permeable damaged points. An electrical current flows between the electrically-conductive layer and the counter-electrode disposed in the test chamber—if a gas-permeable damaged point is present in the electrically non-conductive layer—which serves as an indicator for the gas-permeable damaged point in the electrically non-conductive layer. The electrical gas discharge is maintained during measurement of this current.

DETAILED DESCRIPTION OF THE INVENTION

Figure 1:
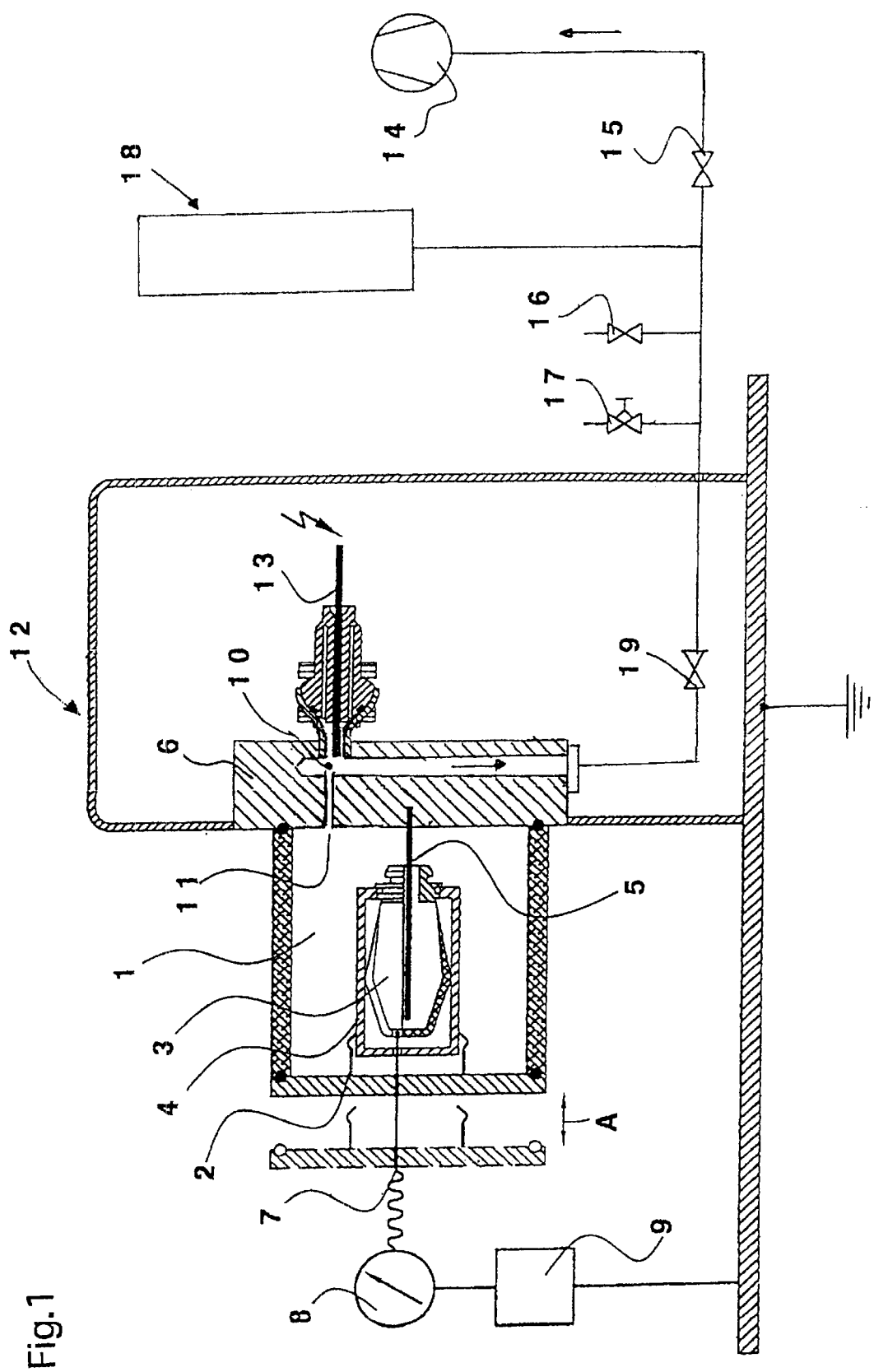
FIG. 1 is a schematic drawing of a test chamber for holding a container-shaped test subject that can be used in the practice of the process of the present invention.

Gas discharge by impact ionisation during dark discharge can on the one hand take place in a gas discharge chamber which is electrically screened from the test chamber and which is connected with the test chamber by means of at least one channel or via a wire grid. Part of the ionized gas is transferred from the gas discharge chamber into the test chamber via the channel or via the wire grid. With this arrangement, only a weak electrical field coming from the high-voltage field in the gas discharge chamber is present within the test chamber, hardly influencing the test current circuit. On the other hand, the gas discharge can take place in the test chamber itself.

In both cases, the ionized gas is only in contact with the side with the non-conductive layer which is adjacent to the gas environment. In the case of a two-layer composite comprising a metal foil coated on one side, the ionized gas in only in contact with the side of the two-layer composite which is provided with the electrically non-conductive layer.

It can be expedient to ionise the gas within the test chamber by means of an electrical gas discharge with DC voltage, and to apply an AC voltage between the electrically-conductive layer and the counter electrode disposed in the test chamber.

Furthermore, it can be expedient to set the voltage in the test current circuit and the gas pressure in the gas environment to values wherein the electrical field strength in the area between the counter-electrode and the electrically-conductive layer lies beneath the dielectric strength of the electrically non-conductive layer without gas-permeable damaged points, and where a recognisable alteration is produced at a gas-permeable damaged point in the electrically non-conductive layer by means of a dielectric breakdown, by which the location of the gas-permeable damaged point is optically marked. In this case, the electrically-conductive layer cannot be used for the intended application. However, optical marking of the damaged points simplifies further investigations relating to the spatial position of the damaged points and the reasons for their existence.

In the ionized gas in the test chamber, an electrical current is produced by placing an electrical voltage between the electrically-conductive layer and the counter-electrode disposed in the test chamber in the event that a gas-permeable damaged point is present in the electrically non-conductive layer which is disposed therebetween. In this case, the ionized gas is in contact with the electrically-conductive layer at the gas-permeable damaged point, and the current in the test current circuit is greater than with an electrically non-conductive layer without gas-permeable damaged point.

The gas discharge is effected by high-voltage electrical energy which can be supplied in a suitable manner by means of electrodes or capacitatively or inductively. Supply by means of electrodes is preferred. The gas discharge can occur by means of DC voltage or AC voltage of 0.5 kV to 10 kV. The frequency of the AC voltage can lie in the low frequency range and is preferably 10 Hz to 30 kHz, especially preferably 40 Hz to 70 Hz. Furthermore, the frequency of the AC voltage can lie in the high frequency range of 30 kHz to 1 GHz, and is preferably 30 kHz to 100 kHz, especially preferably 30 kHz to 40 kHz.

The current flow in the ionized gas in the test chamber can be produced by applying an electrical DC voltage or an electrical AC voltage, preferably an electrical voltage of 50 V to 5000 V, preferably 500 V to 1500 V. The electrical field strength produced by this electrical voltage in the area of the non-conductive layer lies beneath the dielectric strength of the electrically non-conductive layer, without gas-permeable damaged point.

The pressure in the gas environment, which can comprise either the gas discharge chamber and the test chamber or only the test chamber, is between 0.5 hPa to 50 hPa (0.5 mbar to 50 mbar), preferably 1 hPa to 4 hPa (1 mbar to 4 mbar). The gas environment can be filled with nitrogen, a noble gas or preferably with air.

The test subject can be a multi-layer composite and can comprise an electrically-conductive layer and at least one electrically non-conductive layer. The composite can be present as either a composite length or as a composite section. Furthermore, a single electrically non-conductive layer in the form of a film or plate with almost any thickness, lying on one side opposite an electrically-conductive layer, and the gas environment lying opposite on the other side, is suitable as a test piece. In this case, the electrically-conductive layer can be a plate or a pot-shaped lid made of metal, with which the test chamber is sealed in a gas-tight manner. The metal plate can touch the electrically non-conductive layer on the one side, or it can be disposed at a preferably small distance from the one side of the electrically non-conductive layer.

Furthermore, the test subject can be a container produced from a multi-layer composite or from a single electrically non-conductive layer, which has an opening. Such containers can, for example, comprise a relatively thick and thus rigid multi-layer composite, or a rigid plastic, and are approximately form-stable, or they can comprise a relatively-thin multi-layer composite or a relatively-thin plastic film, and can be collapsible. Furthermore, a miniaturised form-stable metal container with electrically non-conductive inner coating is suitable. Such containers are used for packaging sensitive pharmaceutical products.

The shape of the test chamber is adapted to the shape of the test subject. If the test subject is present in the form of a container, which is provided, for example, with a seam as well as with a flange and an opening which penetrates through the flange, the container, in the area of its flange, is placed tightly into a sample holder provided with an adapted opening which is made of an electrically non-conductive material. The sample carrier serves as a cover for the test chamber and is preferably only slightly larger than the container which is placed therein. The sample carrier includes the container and keeps the ionized gas away from the outside of the container and thus away from the optionally free-lying electrically-conductive layer. The counter-electrode can be pushed into the container through its opening; it generally does not touch the container and the interior wall of the opening in the container flange. The electrical supply to the electrically-conductive layer of the multi-layer composite is guided in a gas-tight manner through the sample carrier and is connected in the environment which is free from ionising gas in the area of the outside of the container with the electrically-conductive layer of the container. In the case of a container which comprises a two-layer composite, wherein the inner side of a metal foil is coated with a plastic film as a non-conductive layer, the electrical supply can be applied to the outside of the metal foil in the area of the seam or in the area of the flange. In the case of a container which comprises a 3-layer composite, wherein the metal foil is coated on both sides with a plastic film as a non-conductive layer, it is preferred that both plastic films and the metal layer are penetrated needle-fashion by the electrical supply, for example in the area of the seam, where upon the electrical contact is provided to the metal layer.

If the test subject is a collapsible foil bag, it can be expedient to keep the free space between the inside of the sample carrier and the outside of the collapsible foil bag at the same gas pressure as in the inside of the foil bag, so that the foil bag is present during examination in non-collapsed form.

Optionally, several containers can be placed next to one another in the test chamber. The test current produced in the ionized gas in the test chamber can be measured separately for each container disposed in the test chamber, or in the case of a parallel circuit, all containers can be measured together.

If the test subject is present in the form of a section of the multi-layer composite, the composite section is placed on the one side of a e.g. disc-shaped sample carrier of electrically non-conductive material, the dimensions of which are adapted to the dimensions of the composite section. The disc-shaped sample carrier and hence the composite section placed thereon is placed tightly against an adapted counter-piece which is provided with an opening, the size of which is adapted to the size of the composite section. The ionized gas is kept away from the side of the multi-layer composite which faces the disc-shaped sample carrier. The counter-electrode is disposed on the side of the multi-level composite which faces the ionized gas, adjacent to the opening in the counter-piece; it generally does not touch the multi-layer composite. The electrical supply can be connected with the electrically-conductive layer of the section of the multi-layer composite in the area of its externally-accessible edge, in a similar manner to examination of a container.

If the test piece is present as a composite length, the composite length can be moved step-wise past the opening in the counter-piece. The composite length can be pressed tightly against the counter-piece, one area after another, by means of a pressure plate, and can be tested one area after another. The counter-electrode is disposed on the side of the composite length which faces the ionized gas. The electrical supply to the electrically-conductive layer of the multi-layer composite can be applied at the edge or at one end of the composite length. In this case, the current flow produced in the ionized gas in the test chamber is measured for, in each case, one area of the multi-layer composite. In this way, gas-permeable damaged points can be detected in the area of the non-conductive layer which is exposed to the ionized gas.

The process according to the invention can, for example, be carried out as follows. A test subject is placed in the test chamber. The test chamber is evacuated to a given gas pressure and is kept at this pressure. The gas is ionized by means of a gas discharge which is electrically screened from the test chamber. The gas discharge is carried out in a gas discharge chamber which is spatially separated from the test chamber. The gas discharge chamber can be connected with the test chamber via a narrow channel or an electrically-conductive wire net can be disposed between the gas discharge chamber and the test chamber. In both cases, an ionized gas is also present in the test chamber as long as the gas discharge is maintained. A test voltage is placed on the electrically-conductive layer of the multi-layer composite and on a counter-electrode. The counter-electrode is disposed within the test chamber which is filled with the ionized gas, preferably in the vicinity of the test subject; it can penetrate into a test subject in the form of a container. The electrical current which flows in the test current circuit via the ionized gas into the test chamber is measured. The magnitude of this current is an indicator for the lack of damage of the non-conductive layer which is exposed to the ionized gas. If the non-conductive layer contains a gas-permeable damaged point at which the electrically-conductive layer of the multi-layer composite is in contact with the ionized gas, the test current is greater than is the case with a plastic layer which contains no gas-permeable damaged points.

The gas pressure and the voltage in the test current circuit can be set to values where a dielectric breakdown occurs at a gas-permeable damaged point in the electrically non-conductive layer. By this, the point of puncture can be modified so that it is visible or measurable, for example blackened, whereupon the gas-permeable damaged point can easily be located.

The test process according to the invention works without contact. The electrically-conductive layer of a multi-layer composite is indeed connected to an electrical supply at a suitable point, for example at the edge of the composite or, in the case of a container, preferably at the seam, but the non-conductive layer which is to be tested is neither in contact with an object (such as the counter-electrode) or a fluid (such as an electrolyte). The non-conductive layer can therefore not be damaged by an object. No residual fluid remains on the non-conductive layer.

The process, according to the invention, works with an ionized and thus electrically-conductive gas (in place of an electrolyte). The gas can be produced by means of gas discharge which is electrically screened from the test chamber. The test subject is disposed outside the gas discharge chamber and is not exposed to the electrical high-voltage field in the gas discharge chamber. The test chamber is connected with the electrically-screened gas discharge chamber either only via a channel or the electrical screening of the gas discharge chamber comprises, on its threshold to the test chamber, an electrically-conductive wire grid or wire mesh. With both arrangements, the gas which is ionized in the gas discharge chamber enters the test chamber and makes the space between the counter-electrode and the electrically non-conductive layer which is to be tested electrically conductive as long as the gas discharge is maintained in the gas discharge chamber. The test current circuit is not affected by the screened high-tension field in the gas discharge chamber.

If the test subject is in the high-voltage field of the gas discharge chamber, measurement of the current in the test current circuit can be affected and the components of the test current circuit can be endangered. Furthermore, for example, a very thin electrically non-conductive layer can be penetrated and damaged. Such difficulties are avoided by the arrangement of the test subject outside the electrically-screened gas discharge chamber.

The gas in the test chamber can also be ionized by means of ionising radiation from a radioactive preparation. This process is less practicable as a result of the required extensive safety measures.

In order to carry out the process according to the invention, an apparatus is suitable wherein an electrically-conductive layer is disposed on the one side of the electrically non-conductive layer, and a gas environment is disposed on the other side of the electrically non-conductive layer. Furthermore, means are provided to evacuate the gas environment. An electrode for producing the gas discharge is disposed within the gas environment. A counter-electrode is provided in the gas environment which forms a test current circuit with a voltage source and a measuring device.

In the case of the first embodiment of the apparatus according to the invention, a gas discharge chamber is provided which forms a part of the gas environment. The gas discharge chamber preferably contains an electrode for producing the gas discharge. The gas discharge chamber is electrically screened from the test chamber. The gas discharge chamber is connected to the test chamber, which forms a further part of a gas environment, by means of at least one channel. Furthermore, means are provided which are attached to the gas discharge chamber and which serve to evacuate and to set the given gas pressure in the gas environment which comprises the gas discharge chamber and the test chamber. The test current circuit contains a voltage source, a display apparatus and the counter-electrode disposed in the test chamber, as well as optionally a protective resistance. The test current circuit serves to measure an electric current flowing though the ionized gas between the electrically-conductive layer and the counter-electrode disposed in the test chamber, if the electrically non-conductive layer contains a gas-permeable damaged point.

In a further embodiment of the apparatus according to the invention, the gas environment comprises the test chamber to which means for evacuating and for setting the given gas pressure in the test chamber are attached. An electrode for producing the electrical gas discharge is disposed in the test chamber. Furthermore, a counter-electrode is disposed in the test chamber, forming a test current circuit with a voltage source and a display apparatus, and optionally with a protective resistance, wherein electrical current flowing through the ionized gas in the test chamber is measured if a gas-permeable damaged point is present in the electrically non-conductive layer.

The display apparatus in the test current circuit can be configured as a switching device which omits a signal or triggers an effect when a given current threshold value is exceeded.

Apart from means for evacuating the gas environment, a pressure compensation vessel can be provided, the volume of which is large in comparison with the volume of the gas environment, and via which rapid evacuation of a gas environment is attained after exchanging test subjects, via which the test chamber is opened. Furthermore, a shutoff valve can be provided in the channel which connects the gas discharge chamber with the test chamber, for example a gas-tight solenoid valve can be provided, this valve being closed when test subjects are exchanged before opening the test chamber, and is opened after closing of the test chamber.

A sample carrier made of an electrically non-conductive material is provided for covering the test subjects which are shaped like a container.

If the test subject is a collapsible container which is to be tested in its non-collapsed state, the free space which lies outside the container and within the cover of the container is also to be evacuated to the given pressure in the gas environment. To this end, this free space is connected with the evacuation apparatus via a line.

In order that no ionized gas can penetrate from the gas environment though this evacuation line, the line can be provided with a valve which, in each case is closed at the end of an evacuation process and is opened again after test subjects have been exchanged at the start of the next evacuation. In the case of short measurement cycles, it can be sufficient to provide a long evacuation line for the free space between the outside of the container and the inside of the container cover so that no ionized gas penetrates into the space outside the container via this circuitous route.

It is expedient to keep the volume of the gas discharged chamber and the test chamber as small as possible. It can furthermore be expedient to provide a pressure equalisation vessel, the volume of which is greater than the volume of the gas discharge chamber and the test chamber together. In this way, the specified pressure in the test chamber can be rapidly set after exchanging test subjects, and a short cycle time in the range of a few seconds can be attained.

In the case of thin non-conductive layers which are sensitive to dialectic breakdown, it can be expedient to select a pressure of less than 1 hPa (less than 1 mbar in the gas environment and a voltage of less than 500 V in the test current circuit.

In the case of thick non-conductive layers which are less sensitive to dielectric breakdown, a relatively high test voltage can be selected.

A combination of higher DC voltage and high-frequency AC voltage can be used to ionise the gas in the gas environment. The process in accordance with the invention and the apparatus in accordance with the invention have the following advantages:

Gas-permeable damaged points which are present in a single layer of electrically non-conductive material, for example in a film or a plate, can be detected, even if these gas-permeable damaged points are fluid-tight.

Gas-permeable damaged points which are present in a multi-layer composite, only in one layer of non-conductive material and not in the layer of conductive material can be detected.

Gas-permeable damaged points in the seam or in the connection point on the container flange can be detected, even if these gas-permeable damaged points are fluid-tight.

The process allows 100% examination of containers or multi-layer composites or of a single electrically non-conductive layer.

Containers produced from a multi-layer composite and also the multi-layer composite itself in the form of sections or in the form of a composite length can be tested for gas-permeable damaged points. The containers can be collapsible or form-stable.

The process works without additives (such as electrolyte) and without touching the electrically non-conductive layer which is to be tested with an electrode.

The process is more sensitive than examination with the help of an electrolyte,

The process can be carried out with air or with another gas contained in the gas environment.

The process can be applied to flat or slightly-bent test subjects and to containers provided with an opening of practically any form and practically any small volume.

The test subjects do not need to be either cleaned or dried after examination.

Sterile test subjects do not need to be re-sterilised after examination.

Short cycle times of examination are attainable.

The apparatus can be configured for fully-automatic operation.

The apparatus can be disposed in a production line for containers of multi-layer composite or upstream of the filling station for such containers.

In cases where there is a low occurrence of gas-permeable damaged points, 100% examination of the containers can be accelerated if a plurality of containers are disposed in the test chamber and are simultaneously examined.

Containers and composite sections with gas-permeable damaged points can be automatically rejected.

The location of the damage on the electrically non-conductive layer can, for example, be made visible by blacking as a result of dielectric breakdown.

With the process of the invention, very small gas-permeable damaged points can be detected in the electrically non-conductive layer which is to be examined, wherein these cannot be detected with other processes, for example with an electrolyte as a conductive medium between the counter-electrode and the conductive layer of the multi-layer composite.

The process according to the invention is more reliable and more sensitive than the process wherein an electrolyte is used. The latter process is, for example, disturbed by air bubbles which adhere inside a container with a seam in the area of the seam and which prevent contact between the electrolyte and the seam at these points. Detection of a gas-permeable damaged point in the area of the seam on which air bubbles adhere is not possible.

The process in accordance with the invention and the apparatus in accordance with the invention are explained in greater detail with reference to the Figures.

FIG. 1 shows a test chamber (1) which is surrounded by side walls and a cover of an electrically-insulating material, for example glass, ceramic or plastic, and which contains a holding apparatus (2) for receiving the container-shaped test subject (3). The test subject (3) is surrounded by the sample carrier (4) as an insulating cover. The holding apparatus (2) in the shape of a resilient bracket, grips the sample carrier (4) of insulating material. By means of the insulating cover, which extends up to the flange of the container-shaped test subject, the cross-sectional edges on the seam of the container-shaped test subject, on which the metal layer of the multi-layer composite lies open, is screened with regard to the space with the ionized gas. The electrical connection to the multi-layer composite does not need to be insulated.

In the case of test subjects without metal cross-sectional edged lying open, the electrically-insulating cover of the test subject can be dispensed with, but then the electrical connection to the multi-layer composite must be covered with regard to the ionized gas. The counter-electrode (5) of the test current circuit projects into the container-shaped test subject (3) through the opening of the container. The counter-electrode is fixed in the housing flange (6). The sample carrier (4) can be axially moved, which is indicated by the arrow A. This allows the test piece to be easily disposed in the sample chamber and easily exchanged. The electrical conduit (7), though which the electrical line is passed for connection of the electrically-conductive layer of the test subject to the test current circuit is disposed in the wall of the test chamber. The test current circuit contains a display apparatus (8) with protective resistance and a test voltage source (9).

The gas discharge chamber (10) is attached to the test chamber (1) and is connected to the test chamber via a channel (11) in the housing flange (6). The channel has a diameter of e.g. 2 mm. The size of the channel cross-section can depend on the volume of the gas discharge chamber. The metal housing (12) for electrical screening of the gas discharge chamber (10) is disposed on the metal housing flange (6). The high-tension electrode (13), which is connected with a high-tension generator (not illustrated) projects into the gas discharge chamber (10).

Furthermore, the apparatus includes a vacuum pump (14), a shutoff valve (15) for the pump, a ventilation valve (16), a dosing valve (17), a pressure equalisation vessel (18) and a shutoff valve (19) for the gas discharge chamber and the test chamber.

After opening the shutoff valve (15) and with the valves (16; 17; 19) closed, the pump (14) begins to evacuate the pressure equalisation vessel (18) and the lines up as far as the closed shutoff valve (19). The specified pressure can either be set by means of a pressure regulator or by means of the dosage valve (17) for introducing air in doses. After disposal of a test subject in the sample chamber, attaching of the conductive layer of the multi-layer composite of the test subject and tight sealing of the sample chamber, the shutoff valve (19) is opened, whereupon in a very short time the specified pressure is set in the gas discharge chamber and in the test chamber. Following this, high voltage of e.g. 2.5 kV is applied to the high voltage electrode (13) and the gas in the gas discharge chamber is ionized. The ionized gas enters the test chamber (1) and the container-shaped test subject (3) through the channel (11).

Whilst maintaining the gas discharge in the gas discharge chamber, the test current flowing through the ionized gas in the test current circuit is read at the display apparatus (8). In the event that the test current lies below a specified threshold value, the test subject is considered to be problem-free with regard to a gas-permeable damaged point in the internal non-conductive layer. If the test current is above the specified threshold value the test subject is rejected as false.

Following this, the valve (19) can be closed, the high voltage is switched off, a further test subject is disposed in the sample chamber and connected to the test current circuit. The valve (19) is opened again and the test cycle is repeated with a further test subject.

Figure 2:
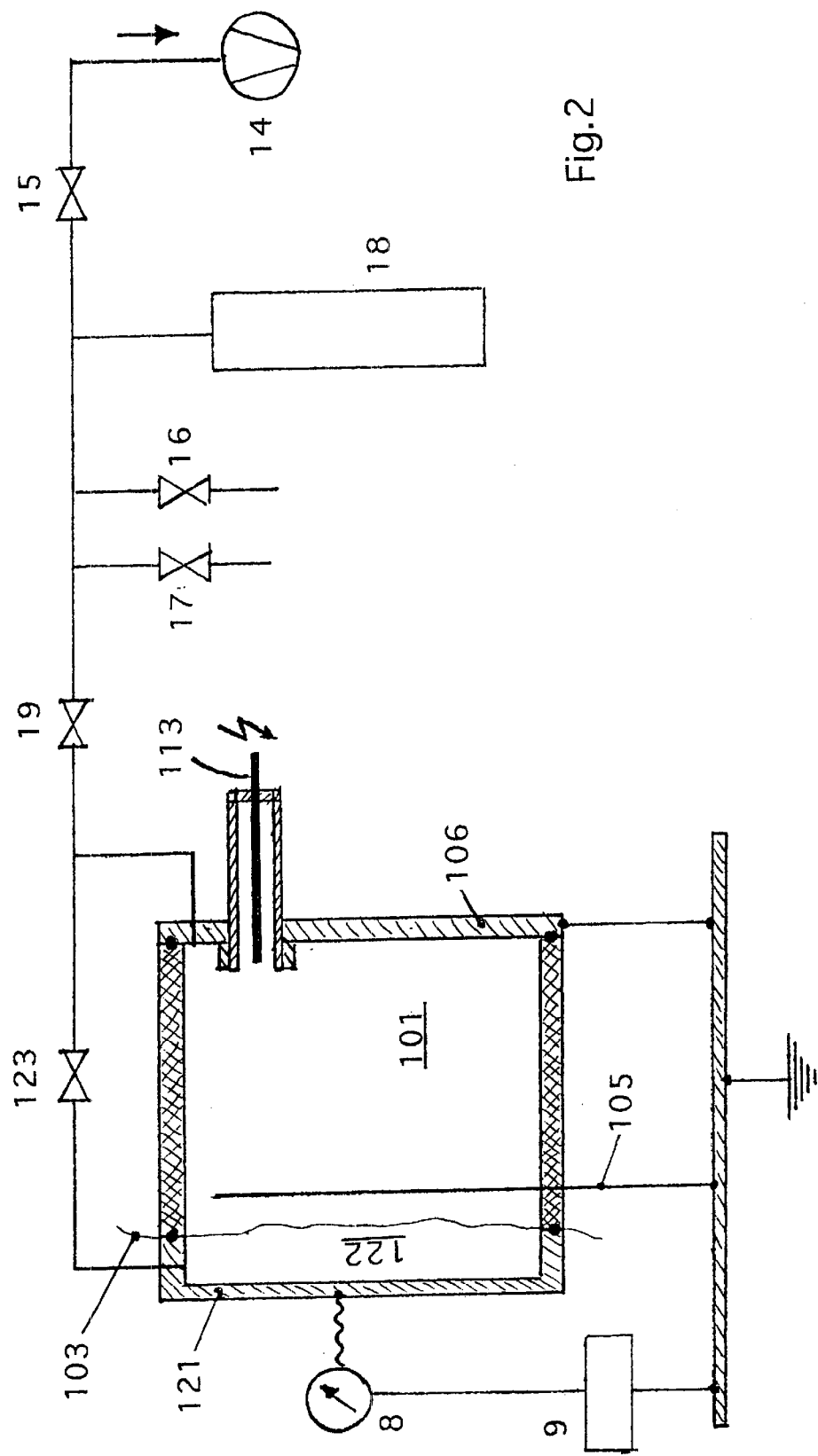
FIG. 2 is a schematic diagram showing an apparatus according to the present invention.

FIG. 2 shows a further embodiment of an apparatus which is suitable for implementing the process according to the invention in an analogous manner to the method outlined hereinbefore. This apparatus does not provide a gas discharge chamber separate from the test chamber (101). The high voltage electrode (113) is disposed in the metal housing base (106) of the test chamber and is not electrically screened from the test chamber. The wall of said chamber comprises an electrically non-conductive material, for example glass, ceramic or plastic. The counter-electrode (105) projects into the test chamber and can be rod-shaped or plate-shaped. The counter electrode lies in the test current circuit with an electrical voltage source (9), a display apparatus (8) and a protective resistance. A test subject (103) is disposed in the test chamber and comprises a single electrically non-conductive layer. On the one side of this layer, the electrically-conductive layer (121) in the form of a pot-shaped metal lid is disposed opposite the test chamber and on the other side is the part of the test chamber in which the gas which is to be ionized is disposed.

A volume (122) can lie between the non-conductive layer (103) and the lid (121) of the test chamber, this volume being filled with a gas which is not directly ionized by the gas discharge. Depending on the type of non-conductive layer (103), the volume (122) is optionally connected via a valve (123) to the evacuation apparatus and is evacuated to the same pressure as the test chamber (101).

The volume (122) can be reduced with a test chamber lid in the form of a flat disc until reaching a negligible remainder. Then it is optionally not necessary to evacuate the volume (122).

The means for evacuating the gas environment (101) and optionally the volume (122) can be configured analogous to FIG. 1.

With the apparatus according to FIG. 2, a distinct current is then measured in the test current circuit if the non-conductive layer (103) contains a gas-permeable damaged point, though which ionized gas passes from the test chamber (103) into the volume (122) and closes the test current circuit.

Table 1 shows measurement results on a plurality of test subjects. These results show the usability of the process according to the invention for detecting gas-permeable damaged points in the test subjects.

Table 1 contains measurement results from the process according to the invention and measurement results by means of a 5% cooking salt solution as an electrolyte, with which each container was filled to the brim. For the electrolyte examination, the same test subjects were used which had hitherto been tested by means of ionized gas. With the electrolyte examination, the ohmic resistance between the conductive layer of the multi-layer composite and an electrode immersed in the electrolyte were measured.

With an undamaged inner layer of the container, the ohmic resistance is infinite. However, a small current can be measured in the test current circuit, even in the case of an undamaged layer, by means of ionized gas.

With the examination by means of electrolyte solution, only test subjects 1 to 4 were evaluated as faulty. With the more sensitive examination according to the invention, test subjects 7, 8, 10, 13 and 14 were also evaluated as faulty in addition to test subjects 1 to 4. Test subjects 5, 6, 9, 11, 12 and 15, which were tested using the process according to the invention, were considered to be free of faults.

With the apparatus according to the invention used for carrying out these measurements, and with consideration for the observed scatter currents, test subjects were considered to be free of faults if a current of less than approximately 0.4 mA was measured in the test current circuit with the process according to the invention.

TABLE 1

| Test subject number | Test with ionised gas Test current mA | Test with electrolyte Resistance MΣ |
|---|---|---|
| 1 | 0.6 | 2.0 |
| 2 | 3.0 | 2.5 |
| 3 | 3.0 | 2.5 |
| 4 | 1.5 | 2.0 |
| 5 | 0.01 | 4 |
| 6 | 0.01 | 4 |
| 7 | 3.0 | 4 |
| 8 | 4.5 | 4 |
| 9 | 0.01 | 4 |
| 10 | 0.5 | 4 |
| 11 | 0.01 | 4 |
| 12 | 0.01 | 4 |
| 13 | 5.0 | 4 |
| 14 | 1.5 | 4 |
| 15 | 0.1 | 4 |

What is claimed is:

1. A process for detecting gas-permeable damaged points in test subjects which comprise an electrically non-conductive layer, wherein an electrically-conductive layer lies opposite the electrically non-conductive layer on the one side and a gas environment lies opposite the electrically non-conductive layer on the other side, wherein The disposal of at least one test subject in a test chamber which has been evacuated to, and maintained at, a given pressure, and Ionisation of the gas by means of an electrical gas discharge in the gas environment on the other side of the electrically non-conductive layer, and Application of an electric voltage between the electrically-conductive layer which lies on one side of the electrically non-conductive layer and a counter-electrode which is disposed in the test chamber, wherein the electrical voltage generates an electrical field strength in the area of the electrically non-conductive layer which lies below the dielectric strength of the electrically non-conductive layer without gas-permeable damaged points, and Measurement of a current flowing though the ionized gas between the electrically-conductive layer and the counter-electrode disposed in the test chamber—in the case of a gas-permeable damaged point being present in the electrically non-conductive layer—which acts as an indicator for the gas-permeable damaged point in the electrically non-conductive layer, with the electrical gas discharge being maintained.

2. A process according to claim 1, wherein

Ionisation of the gas by means of an electrical gas discharge in the gas environment via impact ionisation during dark discharge.

3. A process according to claim 1, wherein

The examination of test subjects which comprise a multi-layer composite with an electrically-conductive layer and at least one electrically non-conductive layer.

4. A process according to claim 1, wherein

The examination of test subjects which exist as a container with an opening and which are produced from a multi-layer composite.

5. A process according to claim 1, wherein

The examination of test subjects which comprise an electrically non-conductive film or plate and on one side of which is disposed an electrically-conductive layer.

6. A process according to claim 1, wherein

A pressure in the ionized gas of 0.5 hPa to 50 hPa (from 0.5 mbar to 50 mbar), preferably 1 hPa to 4 hPa (from 1 mbar to 4 mbar).

7. A process according to claim 1, wherein by

Effecting the gas discharge with high-tension electrical energy which is supplied in a suitable manner, preferably by electrodes.

8. A process according to claim 1, wherein

Effecting the gas discharge with DC voltage of 0.5 kV to 10 kV.

9. A process according to claim 1, wherein

Effecting the gas discharge with AC voltage of 0.5 kV to 10 kV.

10. A process according to claim 9, wherein

Effecting the gas discharge with AC voltage at a frequency of 10 Hz to 30 kHz.

11. A process according to claim 9, wherein

Effecting the gas discharge with high-frequency AC voltage.

12. A process according to claim 11, wherein

Effecting the gas discharge with an AC voltage of 30 kHz to 1 GHz, preferably from 30 kHz to 100 kHz, especially preferably from 30 kHz to 40 kHz.

13. A process according to claim 1, wherein

Generation of the current flow—when a gas-permeable damaged point is present in the electrically non-conductive layer—in the ionized gas in the test chamber by application of an electrical voltage of 50 V to 5000 V, which generates an electrical field strength in the area of the electrically non-conductive layer which lies below the dielectric strength of the electrically non-conductive layer without a gas-permeable damaged point, preferably from 500 V to 1500 V.

14. A process according to claim 1, wherein

Ionisation of the gas by means of an electrical gas discharge within the test chamber by impact ionisation during dark discharge.

15. A process according to claim 14, wherein

Ionisation of the gas by means of an electrical gas discharge with DC voltage within the test chamber and application of an electrical AC voltage between the electrically-conductive layer and the counter-electrode disposed within the test chamber.

16. A process according to claim 1, wherein

Ionisation of the gas by means of an electrical gas discharge within a gas discharge chamber which is electrically screened from the test chamber and which is connected to the test chamber by means of a channel.

17. A process according to claim 16, wherein

Ionisation of the gas by means of an electrical gas discharge within a gas discharge chamber which is electrically screened from the test chamber and which is connected to the test chamber by means of openings in a wire grid.

18. A process according to claim 1, wherein

Setting the gas pressure and the voltage in the test current circuit to values wherein the electrical field strength in the area between the counter-electrode and the electrically-conductive layer lies below the dielectric strength of the electrically non-conductive layer without gas-permeable damaged points, and wherein a recognisable alteration is produced at a gas-permeable damaged point in the electrically non-conductive layer by means of a dielectric breakdown, by which the location of the gas-permeable damaged point is optically marked.

19. A process according to claim 1, wherein

Covering the test subject, which is present as a container, in the test chamber, with a cover which is configured as a sample carrier and which comprises an electrically non-conductive material.

20. A process according to claim 19, wherein

Making the electrical contact to the electrically-conductive layer of a composite of three layers with the inner conductive layer and each of the outer, non-conductive layers by penetrating the three layers in a seam of the container.

21. An apparatus for testing test subjects made from an electrically non-conductive layer for gas-permeable damaged points, wherein an electrically-conductive layer which is disposed on the one side of the electrically non-conductive layer, and a gas environment which is disposed on the other side of the electrically non-conductive layer, and means for evacuating the gas environment, and an electrode which is provided in the gas environment, and a counter-electrode which is provided in the gas environment, and a test current circuit in which the counter-electrode is disposed.

22. An apparatus for testing test subjects according to claim 21, wherein the electrically-conductive layer which is disposed on the one side of the electrically non-conductive layer, and a test chamber (1) which contains the counter-electrode and which is disposed on the other side of the electrically non-conductive layer, and a gas discharge chamber (10) which contains the electrode for producing the gas discharge and which is connected to the test chamber via at least one channel (11), and means (14 to 17), which are connected to the gas discharge chamber, and which serve to evacuate and to set the given gas pressure in the gas environment, comprising the gas discharge chamber and the test chamber, and a voltage source (9) and a display device (8) which, together with the counter-electrode (5), form the test current circuit, which serves to measure a current flowing through the ionized gas between the electrically-conductive layer and the counter-electrode disposed in the test chamber—in the presence of a gas-permeable damaged point in the electrically non-conductive layer, and an electrical screen (12) of the gas discharge chamber.

23. An apparatus for testing test subjects according to claim 21, wherein a test chamber (101) as a gas environment, to which means (14 to 17) are connected for evacuating and for setting the given gas pressure in the test chamber, and the electrode (113) disposed within the test chamber for producing an electrical gas discharge, and the counter-electrode (105) disposed within the test chamber, which is connected to a voltage source (9) and a display device (8) for measuring a current flowing through the ionized gas between the electrically-conductive layer (121) and the counter-electrode (105) disposed in the test chamber—in the presence of a gas-permeable damaged point in the electrically non-conductive layer.

24. An apparatus according to claim 23, wherein
the display device (8), which is configured as a switching device, and which omits a signal or triggers an effect when a given current threshold value is exceeded in the test current circuit.

25. An apparatus according to claim 23, wherein
a pressure compensation vessel (18).

26. An apparatus according to claim 22, wherein
a shutoff valve in the channel (11) between the gas discharge chamber and the test chamber.

27. An apparatus according to claim 23, wherein
a cover (4) which is configured as a sample carrier for a container and which comprises an electrically non-conductive material.

* * * * *